United States Patent
Miyazaki et al.

(10) Patent No.: US 6,638,523 B1
(45) Date of Patent: Oct. 28, 2003

(54) METHOD OF TREATING ULCERS

(75) Inventors: Toshitsugu Miyazaki, Kobe (JP); Kunio Kosaka, Kobe (JP); Hisatomi Ito, Kobe (JP)

(73) Assignee: Nagase & Company, Ltd., Osaka (JP)

( * ) Notice: Subject to any disclaimer, the term of this patent is extended or adjusted under 35 U.S.C. 154(b) by 18 days.

(21) Appl. No.: 09/696,183

(22) Filed: Oct. 26, 2000

(30) Foreign Application Priority Data

Oct. 27, 1999 (JP) .......................................... 11-305383

(51) Int. Cl.[7] ........................ A61K 47/00; A61K 35/78; A01N 65/00; A01N 25/00
(52) U.S. Cl. ..................... 424/439; 424/725; 424/745; 424/746; 514/925; 514/927
(58) Field of Search ............................. 424/439, 78.01, 424/745, 746, 725; 514/925, 927

(56) References Cited

U.S. PATENT DOCUMENTS

| | | | |
|---|---|---|---|
| 4,450,097 A | 5/1984 | Nakatani et al. | 252/404 |
| 5,023,017 A | 6/1991 | Todd, Jr. | 252/407 |
| 5,560,912 A | * 10/1996 | Neeman et al. | 424/195.1 |
| 5,738,850 A | * 4/1998 | Hendricks et al. | 424/195.1 |
| 6,117,868 A | * 9/2000 | Pfirrmann | 514/222.5 |

FOREIGN PATENT DOCUMENTS

| | | |
|---|---|---|
| JP | 03-197595 | 8/1991 |
| JP | 04-013630 | 1/1992 |
| JP | 04-018026 | 1/1992 |
| JP | 04-173070 | 6/1992 |
| JP | 04-247054 | 9/1992 |
| JP | 07-187988 | 7/1995 |
| JP | 08-109122 | 4/1996 |
| JP | 08-119872 | 5/1996 |
| JP | 08-310923 | 11/1996 |

OTHER PUBLICATIONS

"Pyloric campylobacter infection and gastroduodenal disease", by Marshall, Barry J. et al.; Medical Journal of Australia, 1995; vol. No. 142; pp. 439–444.*
"Medical Herb"; Sage (salvia); p. 95, 1995; Japan Vorg Company.
"Aromatopia"; Effectiveness of rosemary in aromatotherapy; p. 47; 1995, Fragrance Journal Ltd.
British Herbal Pharmacopoeia; 1983; p. 180–181; (compile version).
Offord et al., Rosemary components inhibit benzo [$\alpha$]pyrene–induced genotoxicity in human bronchial cells, Carcinogenesis vol. 16, No. 9, P2057–2062, (1995).
Paris et al., Inhibitory effect of carnosolic acid on HIV–1 protease in cell–free assays, J. Natural Products, vol. 56, No. 8, P1426–1430, (1993).
Huang et al., Inhibition of skin tumorigenesis by rosemary and its constituents carnosol and ursolic acid, Cancer Res. Feb. No. 54, P701–708 (1994).
Smith et al., Protection by albumin against the pro–oxidant actions of phenolic dietary components, Food Chem. Toxic, vol. 30, No. 6, P483–489 (1992).

(List continued on next page.)

Primary Examiner—Thurman K. Page
Assistant Examiner—Humera N. Sheikh
(74) Attorney, Agent, or Firm—Jacobson Holman PLLC

(57) ABSTRACT

A method of treating ulcers comprising administering an effective amount of carnosic acid and/or carnosol or a plant extract containing carnosic acid and/or carnosol as an effective ingredient to a subject having such ulcers.

12 Claims, 2 Drawing Sheets

OTHER PUBLICATIONS

Aruma et al., An evaluation of the antioxidant and antiviral action of extracts of rosemary and provencal herbs, Food Chem. Toxic, No. 34, P449–456 (1996).

Pearson et al., Inhibition of endothelial cell–mediated oxidation of low–density lipoprotein by rosemary and plant phenolics, J. Agric. Food Chem., No. 45, P578–582 (1997).

Chan et al., Effects of three dietary phytochemicals from tea, rosemary and turmeric on inflammation–induced nitrite production, Cancer Lett, vol. 96, No. 1, P23–29 (1995).

Laughton et al., Inhibition of mammalian 5–lipoxygenase and cyclo–oxygenase by flavonoids and phenolic dietary additives, Biochem. Pharmacol., vol. 42, No. 9, P1673–81 (1991).

* cited by examiner

METHOD OF TREATING ULCERS

FIELD OF THE INVENTION

The present invention relates to a method of treating ulcers comprising administering an effective amount of a particular ingredient contained in a certain plant, for example plants belonging to the Labiatae family, as an effective ingredient to a subject having such ulcers.

DESCRIPTION OF THE PRIOR ART

Rosemary, alternatively referred to as "Mannenrou", which is a plant belonging to the Labiatae family, is widely used in the West as a herb for medicinal, fragrant and cooking purposes. The effectiveness of rosemary when used for medicinal purposes has been variously described for a long time. For example, the compile version (1983) of the British Herbal Pharmacopoeia has described that rosemary has carminative, analgesic, microbicidal, antiseptic, abirritant, diuretic, antimicrobial effects and the like. Also, according to recent Japanese patent publications, a deodorant effect (JP-A-04/173070), an anti-caries effect (JP-A-04/13630), an antioxidant effect (JP-A-03/197595), antiviral and antineoplastic effects (JP-A-04/247054), and a hair growth stimulating effect (JP-A-04/18026) have been disclosed. Furthermore, various effects of an essential oil of rosemary have been numerously reported in the past (for example, the effectiveness of rosemary in aromatotherapy, aromatopia, No.4, p.47). In addition, effects of several components contained in rosemary have been also clarified. For example, Japanese patent publication JP-A-08/119872 clarifies that a Helicobacter growth-inhibiting effect of rosemary extract is attributable to rosmanol or carvacrol contained in the extract.

It is also known that sage, alternatively referred to as "salvia", which is a plant belonging to the Labiatae family, has carminative, antispasmodic, astringent, microbicidal, angiotelectasis, and hypoglycemic effects and the like ("Medical Herb", Japan Vorg Company). Furthermore, according to recent Japanese patent publications, a sage extract is used in testosterone 5α reductase inhibitors (JP-A-08/310923), skin cosmetics (JP-A-08/109122), metanogenesis inhibitors (JP-A-07/187988) and the like.

The present inventors have intensively searched for a plant extract having a potent curing or prophylactic effect against ulcers such as alcoholic ulcers and stress ulcers, and also intended to clarify effective ingredients contained therein.

SUMMARY OF THE INVENTION

The present inventors found, as a consequence of an intensive search, that rosemary and sage extracts have extremely potent curing and prophylactic effects against ulcers. Furthermore, the present inventors found that their effective ingredients are carnosic acid of the formula (I) below and carnosol of the formula (II) below.

Thus, the present invention provides a method of treating ulcers comprising administering an effective amount of carnosic acid and/or carnosol or a plant extract containing carnosic acid and/or carnosol as an effective ingredient to a subject having such ulcers.

Carnosic acid and/or carnosol or a plant extract containing carnosic acid and/or carnosol may be administered in the form of a drug, quasi-drug or food composition.

Also, the present invention provides a method of producing anti-ulcer drug and quasi-drug compositions comprising formulating an effective amount of carnosic acid and/or carnosol or a plant extract containing carnosic acid and/or carnosol as an effective ingredient.

Furthermore, the present invention provides a food composition comprising carnosic acid and/or carnosol, and a method of producing the food composition comprising formulating carnosic acid and/or carnosol.

DETAILED DESCRIPTION OF THE INVENTION

Figure 1:
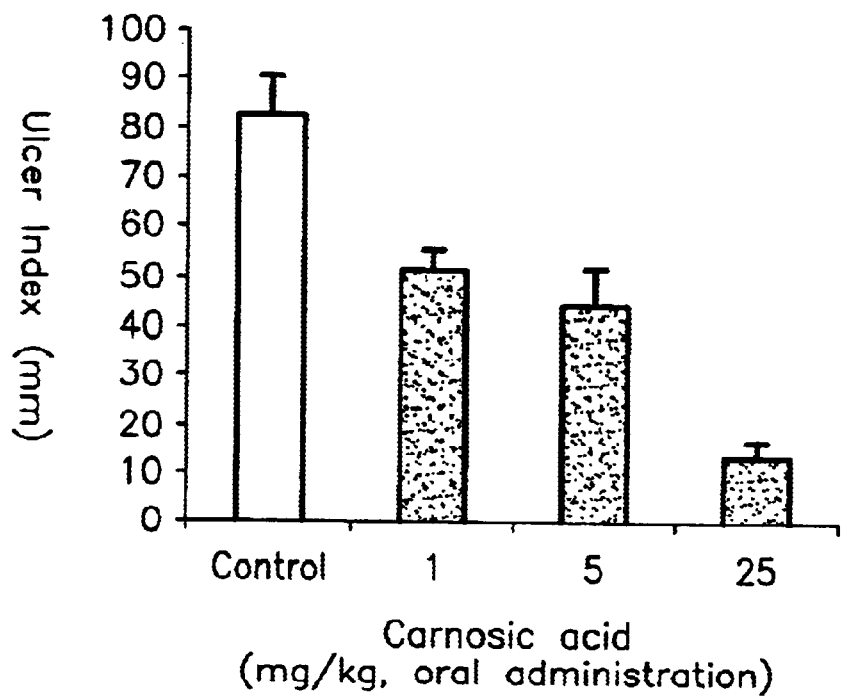
FIG. 1 is a graph showing an anti-ulcer action of carnosic acid.

Carnosic acid of the above formula (I) and carnosol of the above formula (II) are known compounds. Thus, these compounds can be prepared by synthesis.

Alternatively, since these compounds are contained in various plants, they can be obtained by extraction from plants. In particular, these compounds are contained in a plant belonging to the Labiatae family such as rosemary or sage in a large amount, and therefore, they can be easily obtained by extraction from these plants.

The extraction from plants may be carried out in the following manner, for example. The whole plant, leaves and/or petals of rosemary (*Rosmarinus officinalis* L.) or sage (*Salvia officinalis* L.) are soaked in an extraction solvent, and the effective ingredients in the plant are extracted at ordinary temperature, elevated temperature or reflux temperature. The plant residue is filtered off and the resultant extract is concentrated. The concentrate may be separated and purified by various column chromatographic means to obtain the compounds of the above formulas (I) and (II). In the present invention, it is preferable that the extract is obtained from the whole plant in order to improve the productivity.

Solvents for extraction may be conventional solvents used for plant extraction. Organic solvents such as alcohols (methanol, ethanol, etc.) or an aqueous alcohol, also acetone and ethyl acetate may be used alone or in combination with one another. It is preferable to use methanol or ethanol.

Carnosic acid and/or carnosol thus obtained may be administered to a subject having ulcers in the form of a drug, quasi-drug or food composition. Also, a plant extract containing carnosic acid and/or carnosol may be administered to a subject having ulcers. In particular, if a food composition is administered to a subject, the composition preferably contains a plant extract. In such a case, it is preferable to use a rosemary or sage extract.

Examples of drug compositions are tablets, capsules, granules, syrups and the like. The drug compositions may be produced using conventional additives in the production of the drug compositions. Specific examples of the additives are lactose, dextrin, sucrose, mannitol, corn starch, sorbitol, crystalline cellulose, polyvinylpyrrolidone and the like. These materials may be used alone or in suitable combination with one another. The drug compositions may be produced by a conventional process suitable for respective drug compositions. If necessary, it is also possible to use flavoring agents, coloring agents, sweetening agents and the like.

Examples of quasi-drug compositions are tablets, capsules, granules, jellies, drinks and the like. The quasi-drug compositions may be produced using conventional additives in the production of the quasi-drug compositions. The quasi-drug compositions may also contain other effective ingredients such as vitamins. Furthermore, additives such as sweetening agents, flavoring agents, coloring agents and antioxidants may be used alone or in suitable combination with one another. The quasi-drug compositions may be produced by a process well known to those skilled in the art.

Examples of food compositions are noodles, pasta, granules, tablets, jellies, liquids (drinks) and the like. The food compositions may be produced using various food materials suitably. Specific examples of the food materials are rice, wheat, corn, potato, sweet potato, soybean flour, seaweed (sea tangle, wakame (*Undaria pinnatifida*), agar-agar, etc.) flour, starch syrup, lactose, glucose, fructose, sucrose, mannitol and the like. These materials may be used alone or in suitable combination with one another. The food compositions may be made up into a desired shape, if necessary, by adding water or the like. In addition, flavoring agents, coloring agents, sweetening agents, edible oils, vitamins and the like may be suitably added to the food compositions.

The food compositions of the present invention include an effective amount of carnosic acid of the above formula (I) and/or carnosol of the above formula (II). The effective amount of carnosic acid and/or carnosol is normally about 0.05% by weight to about 20% by weight, preferably about 0.1% by weight to about 10% by weight, more preferably about 0.5% by weight to about 5% by weight, based on the total weight of the food composition.

If the amount of carnosic acid and/or carnosol is less than 0.05% by weight, the food composition can not have an excellent anti-ulcer effect. On the other hand, if the amount of carnosic acid and/or carnosol is more than 20% by weight, the production cost of the food composition is increased but the anti-ulcer effect can not be further improved.

By adding the above amount of carnosic acid and/or carnosol, the food composition of the present invention exhibits a good digestion due to the anti-ulcer action of carnosic acid and carnosol.

Rosemary or sage extracts containing carnosic acid and/or carnosol have been taken as a medical decoction for a long time. Accordingly, no disorder occurs even if carnosic acid and/or carnosol are taken in a large amount. However, the oral dose level per day of the above compounds, by which the development of effects against ulcers is expected, is preferably about 0.01 to about 1000 mg; more preferably about 0.1 to about 500 mg, per kg body weight. The does level is comparable with that of Kelnac (100 mg/kg), benexate (300 mg/kg), nizatidine (0.3~150 mg/kg) or the like, known as an anti-ulcer agent.

EXAMPLES

The present invention is illustrated in more detail based on the following examples, but it is not limited thereto.

Example 1

Rosemary (whole plant, 5 kg) was soaked in ethanol (20 L), and allowed to stand overnight. Plant bodies of rosemary were filtered off and the filtrate was concentrated. Purified water (2 L) was added to the resultant concentrate (1 L) and the precipitate deposited was filtered. The precipitate (rosemary extract) (105 g) was subjected to a silica gel column chromatography (ethyl acetate:hexane (1:4) mixture was used as a developing solvent) to obtain 1.5 g of carnosic acid of the above formula (I) and 0.5 g of carnosol of the above formula (II), respectively. The results of measuring $^{13}C$ and $^{1}H$ NMR spectra ($CDCl_3$) of the resultant compounds are shown in the following Tables 1 and 2.

TABLE 1

$^{13}C$ and $^{1}H$ NMR spectra of carnosic acid

| Carbon atom number | $^{13}C$ $\delta$(ppm) | $^{1}H$ $\delta$(ppm) | |
|---|---|---|---|
| 1 | 34.4(t) | 1.24(1H,m) | 3.29(1H,m) |
| 2 | 20.3(t) | 1.60(1H,m) | 1.75(1H,m) |
| 3 | 41.8(t) | 1.32(1H,m) | 1.50(1H,dt) |
| 4 | 34.4(s) | | |
| 5 | 54.0(d) | 1.57(1H,dd) | |
| 6 | 18.9(t) | 1.86(1H,m) | 2.36(1H,m) |
| 7 | 31.5(t) | 2.85(2H,m) | |
| 8 | 129.0(s) | | |
| 9 | 122.1(s) | | |
| 10 | 48.7(s) | | |
| 11 | 142.1(s) | | |
| 12 | 141.4(s) | | |
| 13 | 133.8(s) | | |
| 14 | 119.4(d) | 6.64(1H,s) | |
| 15 | 27.2(d) | 3.17(1H,m) | |
| 16 | 22.1(q) | 1.21(3H,d) | |
| 17 | 22.5(q) | 1.20(3H,d) | |
| 18 | 32.6(q) | 0.89(3H,s) | |
| 19 | 21.7(q) | 1.00(3H,s) | |
| 20 | 183.1(s) | | |
| | | 6.56(2H,s) | |
| | | 7.36(1H,s) | |

TABLE 2

$^{13}C$ and $^{1}H$ NMR spectra of carnosol

| Carbon atom number | $^{13}C$ $\delta$(ppm) | $^{1}H$ $\delta$(ppm) | |
|---|---|---|---|
| 1 | 30.0(t) | 2.81(1H,m) | 2.51(1H,td) |
| 2 | 19.9(t) | 1.97(1H,m) | 1.533(1H,m) |
| 3 | 42.2(t) | 1.27(1H,m) | 1.474(1H,m) |
| 4 | 35.2(s) | | |
| 5 | 46.5(d) | 1.64(1H,dd) | |
| 6 | 30.8(t) | 1.77(1H,m) | 2.144(1H,m) |
| 7 | 78.1(d) | 5.28(2H,dd) | |
| 8 | 123.7(s) | | |
| 9 | 133.2(s) | | |
| 10 | 49.2(s) | | |
| 11 | 144.0(s) | | |
| 12 | 144.1(s) | | |
| 13 | 134.7(s) | | |
| 14 | 112.1(d) | 6.64(1H,s) | |
| 15 | 27.2(d) | 3.22(1H,m) | |
| 16 | 23.0(q) | 1.18(3H,d) | |
| 17 | 23.1(q) | 1.17(3H,d) | |
| 18 | 20.1(q) | 0.87(3H,s) | |
| 19 | 32.2(q) | 0.83(3H,d) | |
| 20 | 175.2(s) | | |
| | | 7.7–7.2(2H,0H) | |

Example 2

To Wistar male rats (5 rats per group) of 180–200 g body weight fasted for 24 hours before the start of a test, carnosic acid obtained in Example 1 was orally administered in dose levels of 1, 5 and 25 mg per kg body weight, after suspending it in water. Similarly, carnosol obtained in Example 1 was orally administered in dose levels of 2.5, 10 and 25 mg per kg body weight, after suspending it in water. After 30 minutes of the administration, 1 ml of ethanol (99.5%) was orally administered to each rat. After one hour of the ethanol administration, laparotomy was carried out and the lengths of all ulcers developed in the stomach were measured and added up. Similar measurements were carried out on the rats of the control group which received ethanol without receiving the above compounds and the result obtained was compared with the above results. These results are shown in FIGS. 1 and 2.

As can be seen from FIG. 1, it was found that carnosic acid of the formula (I) obtained in Example 1 has a potent anti-ulcer action. It was proved that the compound shows $ED_{50}=3.1$ mg/kg (oral administration), and has an extremely potent effect as compared with ebrotidine ($ED_{50}=26.54$ mg/kg) well known as an anti-ulcer compound.

Figure 2:
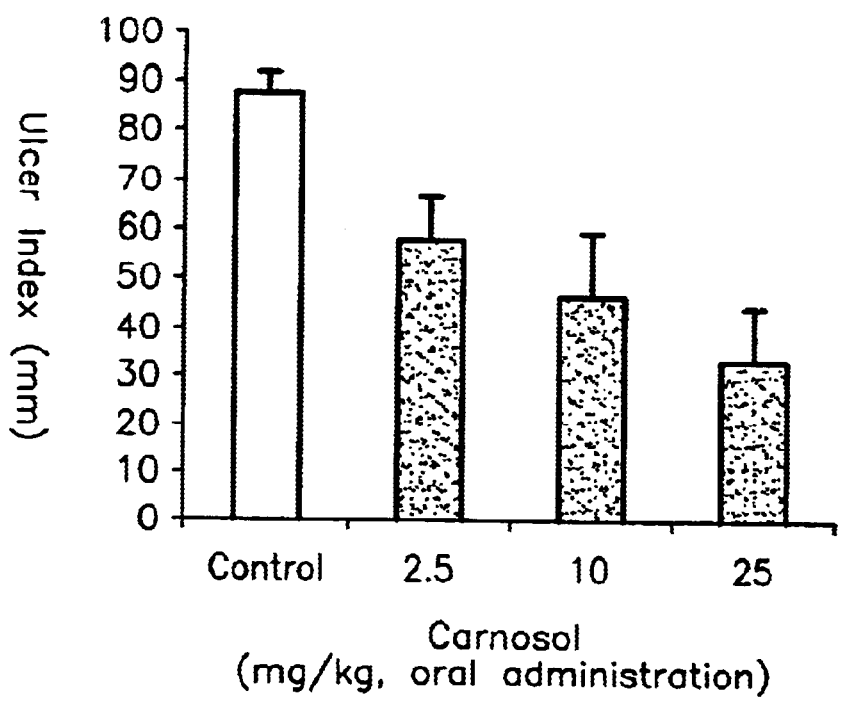
FIG. 2 is a graph showing an anti-ulcer action of carnosol.

As can be seen from FIG. 2, it was also found that carnosol of the formula (II) obtained in Example 1 has a potent anti-ulcer action. It was proved that the compound shows $ED_{50}=9.6$ mg/kg (oral administration), and has a relatively low effect as compared with carnosic acid.

Example 3

To Wistar male rate (5 rats per group) of 180–200 g body weight fasted for 24 hours before the start of a test, the rosemary extract before the column chromatography treatment obtained in Example 1 (containing carnosic acid and carnosol in a high content) was orally administered in a dose level of 50 mg per kg body weight, after suspending it in water. After 30 minutes of the administration, the rats were fixed with a gauge and placed in a water bath at a temperature of 23–24° C. so that the pectoral regions and below of the rats were submerged in water. After 7 hours, laparotomy was carried out and the lengths of all ulcers developed in the stomach were measured and added up. Similar measurements were carried out on the rats of the control group which received a similar treatment without receiving the above extract and the result obtained was compared with the above results. These results are shown in FIG. 3.

Figure 3:
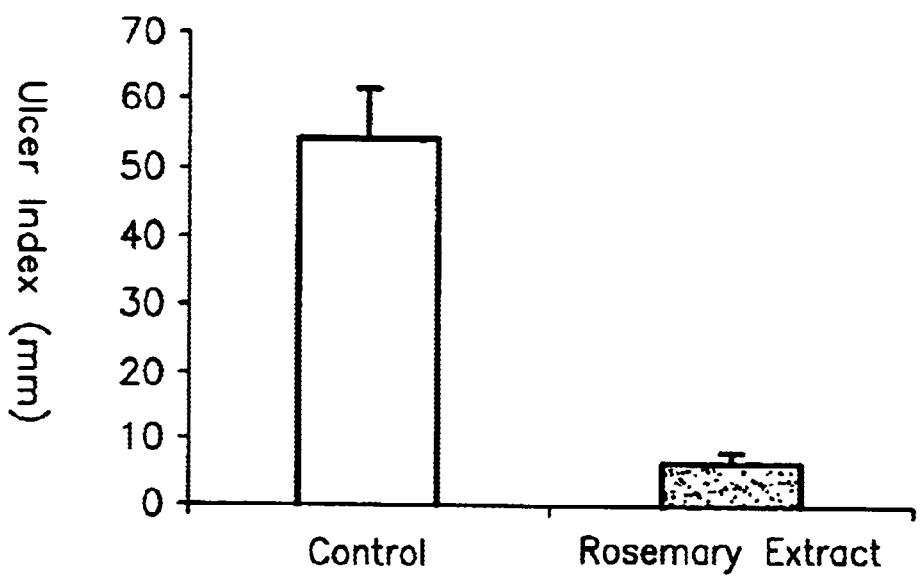
FIG. 3 is a graph showing an anti-ulcer action of a rosemary extract.

As can be seen from FIG. 3, it was found that the rosemary extract has a potent anti-ulcer action.

Example 4

Sage (whole plant, 5 kg) was soaked in ethanol (20 L), and allowed to stand for one day. Plant bodies of sage were filtered off and the filtrate was concentrated. Purified water (2 L) was added to the resultant concentrate (1 L) and the precipitate deposited was filtered. The precipitate was dried to obtain a sage extract (95 g) containing carnosic acid and carnosol in a high content.

The sage extract was mixed with a commercial breeding feed for rats in an amount of 10% of the feed and the mixture was allowed to eat by rats (5 rats per group) freely for one week.

The rats were fasted for 24 hours before the start of a test, and 1 ml of ethanol (99.5%) was orally administered to each rat. After one hour of the ethanol administration, laparotomy was carried out and the lengths of all ulcers developed in the stomach were measured and added up. Similar measurements were carried out on the rats of the control group (5 rats) which were allowed to eat a breeding feed not containing the sage extract and the result obtained was compared with the above results. These results are shown in FIG. 4.

Figure 4:
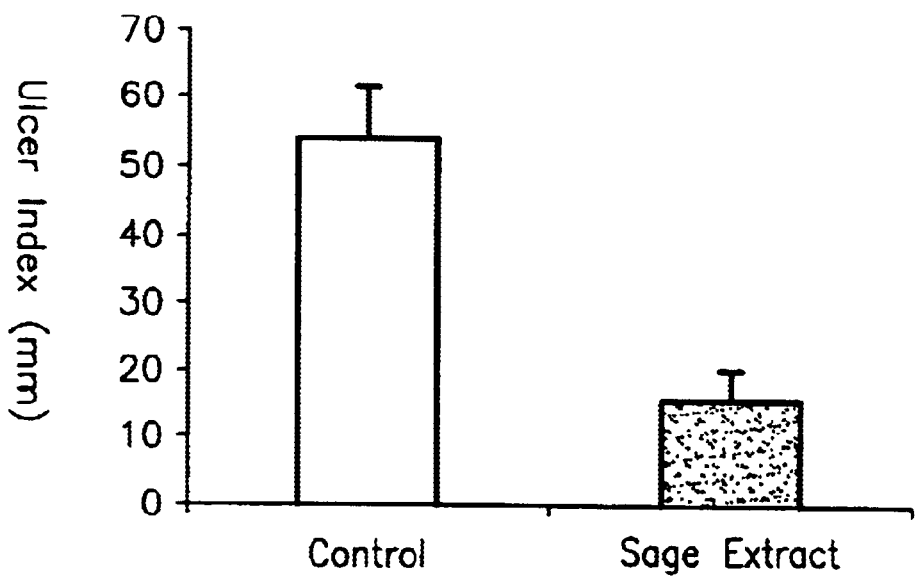
FIG. 4 is a graph showing an anti-ulcer action of a sage extract.

As can be seen from FIG. 4, it was found that the sage extract has a potent anti-ulcer action.

Example 5

Carnosic acid (10 mg), lactose (50 mg) and crystalline cellulose (50 mg) were formulated to obtain a mixture, an aqueous hydroxypropyl cellulose solution was sprayed on the mixture, and fluidized bed granulation of the mixture was carried out to obtain granules. A small amount of magnesium stearate was added to the granules and the resultant granules were filled into capsules.

Example 6

The extract obtained in Example 4 (3 g) and wheat flour (200 g) were charged into a bowl and the materials were thoroughly mixed. An adequate amount of water was added to the mixture and the mixture was kneaded. The resultant rice cake-like products were rolled and shredded to obtain noodle-like products.

According to the present invention, it is possible to mildly treat or prevent ulcers such as alcoholic ulcers and stress ulcers by administering an effective amount of carnosic acid and/or carnosol or a plant extract containing carnosic acid and/or carnosol to a subject having such ulcers.

What is claimed is:

1. A method of treating chemically induced or stress ulcers which comprises administering an effective amount of an active ingredient to a subject having such ulcers, and wherein the active ingredient consists essentially of a member selected from the group consisting of carnosic acid and carnosol.

2. The method according to claim 1 wherein the chemically induced ulcers are alcohol-induced ulcers.

3. The method according to claim 1 wherein the active ingredient is administered in food composition form.

4. A method of treating chemically induced or stress ulcers which comprises administering an effective amount of an active ingredient to a subject having such ulcers, and wherein the active ingredient consists essentially of a rosemary or sage extract comprising a member selected from the group consisting of carnosic and carnosol.

5. The method according to claim 4 wherein the chemically induced ulcers are alcohol-induced ulcers.

6. The method according to claim 4 wherein the rosemary or sage extract is administered in a food composition form.

7. A method of inhibiting development of chemically induced or stress ulcers which comprises administering an effective amount of an active ingredient to a subject, and wherein the active ingredient consists essentially of a member selected from the group consisting of carnosic acid and carnosol.

8. The method according to claim 7 wherein the chemically induced ulcers are alcohol-induced ulcers.

9. The method according to claim 7 wherein the active ingredient is administered in food composition form.

10. A method of inhibiting development of chemically induced or stress ulcers which comprises administering an effective amount of an active ingredient to a subject, and wherein the active ingredient consists essentially of a rosemary or sage extract comprising a member selected from the group consisting of carnosic acid and carnosol.

11. The method according to claim 10 wherein the chemically induced ulcers are alcohol-induced ulcers.

12. The method according to claim 10 wherein the rosemary or sage extract is administered in food composition form.

* * * * *